US006803221B2

(12) United States Patent
Hu et al.

(10) Patent No.: US 6,803,221 B2
(45) Date of Patent: Oct. 12, 2004

(54) HUMAN KINASE AND POLYNUCLEOTIDES ENCODING THE SAME

(75) Inventors: Yi Hu, Spring, TX (US); James Alvin Kieke, Houston, TX (US); Gregory Donoho, Portage, MI (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 10/419,279

(22) Filed: Apr. 17, 2003

(65) Prior Publication Data

US 2003/0225259 A1 Dec. 4, 2003

Related U.S. Application Data

(63) Continuation of application No. 10/014,882, filed on Dec. 11, 2001, now Pat. No. 6,593,126.
(60) Provisional application No. 60/254,744, filed on Dec. 11, 2000.

(51) Int. Cl.[7] .......................... C12N 9/12; C12N 15/00; C12N 5/00; C12N 1/20; C07K 1/00
(52) U.S. Cl. ..................... 435/194; 530/350; 435/320.1; 435/325; 435/252.3
(58) Field of Search .............................. 435/194, 252.3, 435/320.1, 325; 530/350

(56) References Cited

U.S. PATENT DOCUMENTS

| | | | |
|---|---|---|---|
| 4,215,051 A | 7/1980 | Schroeder et al. | |
| 4,376,110 A | 3/1983 | David et al. | |
| 4,594,595 A | 6/1986 | Struckman | |
| 4,631,211 A | 12/1986 | Houghten | |
| 4,689,405 A | 8/1987 | Frank et al. | |
| 4,713,326 A | 12/1987 | Dattagupta et al. | |
| 4,873,191 A | 10/1989 | Wagner et al. | |
| 4,946,778 A | 8/1990 | Ladner et al. | |
| 5,252,743 A | 10/1993 | Barrett et al. | |
| 5,272,057 A | 12/1993 | Smulson et al. | |
| 5,424,186 A | 6/1995 | Fodor et al. | |
| 5,445,934 A | 8/1995 | Fodor et al. | |
| 5,459,127 A | 10/1995 | Felgner et al. | |
| 5,556,752 A | 9/1996 | Lockhart et al. | |
| 5,700,637 A | 12/1997 | Southern | |
| 5,723,323 A | 3/1998 | Kauffman et al. | |
| 5,744,305 A | 4/1998 | Fodor et al. | |
| 5,756,289 A | 5/1998 | Hoekstra | |
| 5,817,479 A | 10/1998 | Au-Young et al. | |
| 5,830,721 A | 11/1998 | Stemmer et al. | |
| 5,837,458 A | 11/1998 | Minshull et al. | |
| 5,869,336 A | 2/1999 | Meyer et al. | |
| 5,877,397 A | 3/1999 | Lonberg et al. | |
| 5,948,767 A | 9/1999 | Scheule et al. | |
| 6,075,181 A | 6/2000 | Kucherlapati et al. | |
| 6,110,490 A | 8/2000 | Thierry | |
| 6,150,584 A | 11/2000 | Kucherlapati et al. | |

FOREIGN PATENT DOCUMENTS

| EP | 1 085 093 A2 A3 | 3/2001 |
|---|---|---|
| WO | WO 01/55356 A2 | 8/2001 |
| WO | WO 01/60991 A2 | 8/2001 |
| WO | WO 01/75067 A2 | 10/2001 |

OTHER PUBLICATIONS

Bird et al, 1988, "Single–Chain Antigen–Binding Proteins", Science 242:423–426.

Bitter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Gordon, 1989, "Transgenic Animals", International Review of Cytology, 115:171–229.

Greenspan et al, 1993, "Idiotypes: structure and immunogenicity", FASEB Journal 7:437–444.

Gu et al, 1994, "Deletion of a DNA Polymerase β Gene Segment in T Cells Using Cell Type–Specific Gene Targeting", Science 265:103–106.

Huse et al, 1989, "Generation of a Large Combinatorial Library of the Immunoglobulin Repertoire in Phage Lambda", Science 246:1275–1281.

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al, 1987, "Sequence–dependent hydrolysis of RNA using modified oligonucleotide splints and R Nase H", FEBS Letters 215(2):327–330.

Inoue et al, 1987, "Synthesis and hyridization studies on two complementary nona(2'–O–methyl)ribonucleotides", Nucleic Acids Research 15(15):6131–6149.

Inouye & Inouye, 1985, "Up–promoter mutations in the Ipp gene of *Escherichia coli*", Nucleic Acids Research 13(9):3101–3110.

Janknecht et al, 1991, "Rapid and efficient purification of native histidine–tagged protein expressed by recombinant vaccinia virus", PNAS 88:8972–8976.

Kohler & Milstein, 1975, "Continuous cultures of fused cells secreting antibody of predefined specilicity", Nature 256:495–497.

(List continued on next page.)

*Primary Examiner*—Maryam Monshipouri

(57) ABSTRACT

Novel human polynucleotide and polypeptide sequences are disclosed that can be used in therapeutic, diagnostic, and pharmacogenomic applications.

1 Claim, No Drawings

OTHER PUBLICATIONS

Lakso et al, 1992, "Targeted oncogene activation by site–specific recombination in transgenic mice", Proc. Natl. Acad. Sci. USA 89:6232–6236.

Lavitrano et al, 1989, "Sperm Cells as Vectors for Introducing Foreign DNA into Eggs: Genetic Transformation of Mice", Cell 57:717–723.

Lo, 1983, "Transformation by Iontophoretic Microinjection of DNA: Multiple Integrations without Tandem Insertions", Mol. Cell. Biology 3(10):1803–1814.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the *Autographa californica* Nuclear Polyhedrosis Virus Genome: Deletion Mutations within the Polyhedrin Gene", J. Virol. 46(2):584–593.

Stein et al, 1988, "Physiochemical properties of phsophorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Thompson et al, 1989, "Germ Line Transmission and Expression of a Corrected HPRT Gene Produced by Gene Targeting in Embryonic Stem Cells", Cell 56:313–321.

Van Der Putten et al, 1985, "Efficient insertion of genes into the mouse germ line via retroviral vectors", Proc. Natl. Acad. Sci. USA 82:6148–6152.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

Database EMBL 'Online', Hall, R., "Human DNA sequence from clone RP5–862P8 on chromosome 1q42.2–43, contains among others, a gene similar to MAP3K10 (mitogen–activated protein kinase kinase kinase 10)," Dec. 08, 1999, database accession No. AL 133380, XP002204715, abstract.

Database Biosis 'Online', KVASHA S.M, et al., "Isolation, expression analysis and chromosomal mapping of a novel human kinase gene MLK4," Biopolimery I Kletka, vol. 17, No. 4, Jul. 2001, pp. 302–307, ISSN: 0233–7657, XP002204714, abstract.

Nagase, T. et al., "Prediction of the coding sequences of unidentified human genes. XX. The complete sequences of 100 new CDNA clones from brain which code for large proteins in vitro," DNA Research, vol. 8, No. 2, 2001, pp. 85–95, XP001030942, ISSN: 1340–2838.

Database EMBL 'Online', UI–HF–EMO–adv–1–12–0–Ul.r1 NIH_MGC_38 Homo sapiens cDNA clone IMAGE: 3062951, Feb. 08, 2000, NIH–MGC, National Institues of Health, Mammalian gene colleciton (MGC), Database accession No. AW 408639, XP002204716, abstract.

Dorow, Donna S. et al., "Complete nucleotide sequence, expression, and chromosomal localisation of human mixed–lineage kinase 2," European Journal of Biochemistry, vol. 234, No. 2, 1995, pp. 492–500, XP001084167, ISSN: 0014–2956.

Dorow, Donna S. et al., "Identification of a new family of human epithelial protein kinases containing two leucine/isoleucine–zipper domains," European Journal of Biochemistry, vol. 213, No. 2, 1993, pp. 701–710, XP001084152, ISSN: 0014–2956.

Gallo, Kathleen A. et al., "Identification and characterization of SPRK, a novel src–homology 3 domain–containing proline–rich kinase with serine/threonine kinase activity," Journal of Biological Chemistry, vol. 269, No. 21, 1994, pp. 15092–15100, XP002204759, ISSN: 02021–9258.

SEQUENCE LISTING

<160> NUMBER OF SEQ ID NOS: 3

<210> SEQ ID NO 1
<211> LENGTH: 3111
<212> TYPE: DNA
<213> ORGANISM: homo sapiens

<400> SEQUENCE: 1

```
atggctttgc ggggcgccgc gggagcgacc gacacccggg tgtcctcggc cggggagcc       60 cccggcggct cagcgtcctc gtcgtccacc tcctcgggcg gctcggcctc ggcgggcgcg      120
gggctgtggg ccgcgctcta tgactacgag gctcgcggcg aggacgagct gagcctgcgg      180
cgcggccagc tggtggaggt gctgtcgcag gacgccgccg tgtcgggcga cgagggctgg      240
tgggcaggcc aggtgcagcg gcgcctcggc atcttccccg ccaactacgt ggctccctgc      300
cgcccggccg ccagccccgc gccgccgccc tcgcggccca gctccccggt acacgtcgcc      360
ttcgagcggc tggagctgaa ggagctcatc ggcgctgggg gcttcgggca ggtgtaccgc      420
gccacctggc agggccagga ggtggccgtg aaggcggcgc gccaggaccc ggagcaggac      480
gcggcggcgg ctgccgagag cgtgcggcgc gaggctcggc tcttcgccat gctgcggcac      540
cccaacatca tcgagctgcg cggcgtgtgc ctgcagcagc cgcacctctg cctggtgctg      600
gagttcgccc gcggcggagc gctcaaccga gcgctggccg ctgccaacgc cgccccggac      660
ccgcgcgcgc ccggcccccg ccgcgcgcgc cgcatccctc cgcacgtgct ggtcaactgg      720
gccgtgcaga tagcgcgggg catgctctac ctgcatgagg aggccttcgt gcccatcctg      780
caccgggacc tcaagtccag caacattttg ctacttgaga agatagaaca tgatgacatc      840
tgcaataaaa ctttgaagat tacagatttt gggttggcga gggaatggca caggaccacc      900
aaaatgagca cagcaggcac ctatgcctgg atggcccccg aagtgatcaa gtcttccttg      960
ttttctaagg gaagcgacat ctggagctat ggagtgctgc tgtgggaact gctcaccgga     1020
gaagtcccct atcggggcat tgatggcctc gccgtggctt atgggtagc agtcaataaa      1080 ctcactttgc ccattccatc cacctgccct gagccgtttg ccaagctcat gaaagaatgc     1140
tggcaacaag accctcatat tcgtccatcg tttgccttaa ttctcgaaca gttgactgct     1200
attgaagggg cagtgatgac tgagatgcct caagaatctt ttcattccat gcaagatgac     1260
tggaaactag aaattcaaca aatgtttgat gagttgagaa caaaggaaaa ggagctgcga     1320
tcccgggaag aggagctgac tcgggcggct ctgcagcaga agtctcagga ggagctgcta     1380
aagcggcgtg agcagcagct ggcagagcgc gagatcgacg tgctggagcg ggaacttaac     1440
attctgatat tccagctaaa ccaggagaag cccaaggtaa agaagaggaa gggcaagttt     1500
aagagaagtc gtttaaagct caaagatgga catcgaatca gtttaccttc agatttccag     1560
cacaagataa ccgtgcaggc ctctcccaac ttggacaaac ggcggagcct gaacagcagc     1620
```

```
agttccagtc ccccgagcag ccccacaatg atgccccgac tccgagccat acagttgact    1680
tcagatgaaa gcaataaaac ttggggaagg aacacagtct ttcgacaaga agaatttgag    1740
gatgtaaaaa ggaattttaa gaaaaaaggt tgtacctggg gaccaaattc cattcaaatg    1800
aaagataaaa cagattgcaa agaaaggata agacctctct ccgatggcaa cagtccttgg    1860
tcaactatct taataaaaaa tcagaaaacc atgcccttgg cttcattgtt tgtggaccag    1920
ccagggtcct gtgaagagcc aaaactttcc cctgatggat tagaacacag aaaaccaaaa    1980
caaataaaat tgcctagtca ggcctacatt gatctacctc ttgggaaaga tgctcagaga    2040
gagaatcctg cagaagctga agctgggag gaggcagcct ctgcgaatgc tgccacagtc     2100
tccattgaga tgactcctac gaatagtctg agtagatccc cccagagaaa gaaaacggag    2160
tcagctctgt atgggtgcac crtccttctg gcatcggtgg ctctgggact ggacctcaga    2220
gakcttcata agcacaggc tgctgaagaa ccgttgccca aggaagagaa gaagaaacga    2280
gagggaatct tccagcgggc ttccaagtcc cgcagaagyg ccagtcctcc cacaagcctg    2340
ccatccacck gtggggaggc cagcagccca ccctccctgc cactgtcaag tgccctgggc    2400
atcctctcca caccttcttt ctccacaaag tgcctgctgc agatggacag tgaagatcca    2460
ctggtggaca gtgcacctgt cacttgtgac tctgagatgc tcactccgga tttttgtccc    2520
actgccccag gaagtggtcg tgagccagcc ctcatgccaa gacttgacac tgattgtagt    2580
gtatcaagaa acttgccgtc ttccttccta cagcagacat gtgggaatgt accttactgt    2640
gcttcttcaa aacatagacc rtcacatcac agacggacca tgtctgatgg aaatccgacc    2700
ccaactggtg caactattat ctcagccact ggagcctctg cactgccact ctgcccctca    2760
cctgmtcytc acwgtcatct gccaaggag gtctcaccca agaagcacag cactgtccac    2820
atcgtgcctc agcgtcgccc tgcctccctg agaagccgct cagatctgcc tcaggcttac    2880
ccacagacag cagtgtctca gctggcacag actgcctgtg tagtgggtcg cccaggacca    2940
catcccaccc aattcctcgc tgccaaggag agaactaaat cccatgtgcc ttcattactg    3000
gatgctgacg tggaaggtca gagcagggac tacactgtgc cactgtgcag aatgaggagc    3060
aaaaccagcc ggccatctat atatgaactg gagaaagaat tcctgtctta a             3111
```

<210> SEQ ID NO 2
<211> LENGTH: 1036
<212> TYPE: PRT
<213> ORGANISM: homo sapiens
<220> FEATURE:
<221> NAME/KEY: VARIANT
<222> LOCATION: (1)...(1036)
<223> OTHER INFORMATION: Xaa = Any Amino Acid

<400> SEQUENCE: 2

```
Met Ala Leu Arg Gly Ala Ala Gly Ala Thr Asp Thr Pro Val Ser Ser
 1               5                  10                  15

Ala Gly Gly Ala Pro Gly Gly Ser Ala Ser Ser Ser Thr Ser Ser
                20                  25                  30

Gly Gly Ser Ala Ser Ala Gly Ala Gly Leu Trp Ala Ala Leu Tyr Asp
            35                  40                  45

Tyr Glu Ala Arg Gly Glu Asp Glu Leu Ser Leu Arg Arg Gly Gln Leu
        50                  55                  60

Val Glu Val Leu Ser Gln Asp Ala Ala Val Ser Gly Asp Glu Gly Trp
65                  70                  75                  80

Trp Ala Gly Gln Val Gln Arg Arg Leu Gly Ile Phe Pro Ala Asn Tyr
                85                  90                  95
```

-continued

```
Val Ala Pro Cys Arg Pro Ala Ser Pro Ala Pro Pro Ser Arg
            100                 105             110
Pro Ser Ser Pro Val His Val Ala Phe Glu Arg Leu Glu Leu Lys Glu
            115                 120             125
Leu Ile Gly Ala Gly Gly Phe Gly Gln Val Tyr Arg Ala Thr Trp Gln
            130                 135             140
Gly Gln Glu Val Ala Val Lys Ala Ala Arg Gln Asp Pro Glu Gln Asp
145                 150                 155                 160
Ala Ala Ala Ala Glu Ser Val Arg Arg Glu Ala Arg Leu Phe Ala
                    165                 170             175
Met Leu Arg His Pro Asn Ile Ile Glu Leu Arg Gly Val Cys Leu Gln
            180                 185             190
Gln Pro His Leu Cys Leu Val Leu Glu Phe Ala Arg Gly Gly Ala Leu
            195                 200             205
Asn Arg Ala Leu Ala Ala Ala Asn Ala Ala Pro Asp Pro Arg Ala Pro
210                 215                 220
Gly Pro Arg Arg Ala Arg Arg Ile Pro Pro His Val Leu Val Asn Trp
225                 230                 235                 240
Ala Val Gln Ile Ala Arg Gly Met Leu Tyr Leu His Glu Glu Ala Phe
                    245                 250             255
Val Pro Ile Leu His Arg Asp Leu Lys Ser Ser Asn Ile Leu Leu Leu
            260                 265             270
Glu Lys Ile Glu His Asp Asp Ile Cys Asn Lys Thr Leu Lys Ile Thr
            275                 280             285
Asp Phe Gly Leu Ala Arg Glu Trp His Arg Thr Thr Lys Met Ser Thr
    290                 295             300
Ala Gly Thr Tyr Ala Trp Met Ala Pro Glu Val Ile Lys Ser Ser Leu
305                 310                 315                 320
Phe Ser Lys Gly Ser Asp Ile Trp Ser Tyr Gly Val Leu Leu Trp Glu
                325                 330             335
Leu Leu Thr Gly Glu Val Pro Tyr Arg Gly Ile Asp Gly Leu Ala Val
            340                 345             350
Ala Tyr Gly Val Ala Val Asn Lys Leu Thr Leu Pro Ile Pro Ser Thr
            355                 360             365
Cys Pro Glu Pro Phe Ala Lys Leu Met Lys Glu Cys Trp Gln Gln Asp
            370                 375             380
Pro His Ile Arg Pro Ser Phe Ala Leu Ile Leu Glu Gln Leu Thr Ala
385                 390                 395                 400
Ile Glu Gly Ala Val Met Thr Glu Met Pro Gln Glu Ser Phe His Ser
                    405                 410             415
Met Gln Asp Asp Trp Lys Leu Glu Ile Gln Gln Met Phe Asp Glu Leu
            420                 425             430
Arg Thr Lys Glu Lys Glu Leu Arg Ser Arg Glu Glu Leu Thr Arg
            435                 440             445
Ala Ala Leu Gln Gln Lys Ser Gln Glu Glu Leu Leu Lys Arg Arg Glu
            450                 455             460
Gln Gln Leu Ala Glu Arg Glu Ile Asp Val Leu Glu Arg Glu Leu Asn
465                 470                 475                 480
Ile Leu Ile Phe Gln Leu Asn Gln Glu Lys Pro Lys Val Lys Lys Arg
                    485                 490             495
Lys Gly Lys Phe Lys Arg Ser Arg Leu Lys Leu Lys Asp Gly His Arg
            500                 505             510
```

```
Ile Ser Leu Pro Ser Asp Phe Gln His Lys Ile Thr Val Gln Ala Ser
        515                 520                 525

Pro Asn Leu Asp Lys Arg Arg Ser Leu Asn Ser Ser Ser Ser Ser Pro
        530                 535                 540

Pro Ser Ser Pro Thr Met Met Pro Arg Leu Arg Ala Ile Gln Leu Thr
545                 550                 555                 560

Ser Asp Glu Ser Asn Lys Thr Trp Gly Arg Asn Thr Val Phe Arg Gln
                565                 570                 575

Glu Glu Phe Glu Asp Val Lys Arg Asn Phe Lys Lys Gly Cys Thr
            580                 585                 590

Trp Gly Pro Asn Ser Ile Gln Met Lys Asp Arg Thr Asp Cys Lys Glu
        595                 600                 605

Arg Ile Arg Pro Leu Ser Asp Gly Asn Ser Pro Trp Ser Thr Ile Leu
        610                 615                 620

Ile Lys Asn Gln Lys Thr Met Pro Leu Ala Ser Leu Phe Val Asp Gln
625                 630                 635                 640

Pro Gly Ser Cys Glu Glu Pro Lys Leu Ser Pro Asp Gly Leu Glu His
                645                 650                 655

Arg Lys Pro Lys Gln Ile Lys Leu Pro Ser Gln Ala Tyr Ile Asp Leu
            660                 665                 670

Pro Leu Gly Lys Asp Ala Gln Arg Glu Asn Pro Ala Glu Ala Glu Ser
        675                 680                 685

Trp Glu Glu Ala Ala Ser Ala Asn Ala Ala Thr Val Ser Ile Glu Met
        690                 695                 700

Thr Pro Thr Asn Ser Leu Ser Arg Ser Pro Gln Arg Lys Lys Thr Glu
705                 710                 715                 720

Ser Ala Leu Tyr Gly Cys Thr Val Leu Ala Ser Val Ala Leu Gly
                725                 730                 735

Leu Asp Leu Arg Glu Leu His Lys Ala Gln Ala Ala Glu Pro Leu
        740                 745                 750

Pro Lys Glu Glu Lys Lys Arg Glu Gly Ile Phe Gln Arg Ala Ser
        755                 760                 765

Lys Ser Arg Arg Ser Ala Ser Pro Pro Thr Ser Leu Pro Ser Thr Gly
        770                 775                 780

Gly Glu Ala Ser Ser Pro Pro Ser Leu Pro Leu Ser Ser Ala Leu Gly
785                 790                 795                 800

Ile Leu Ser Thr Pro Ser Phe Ser Thr Lys Cys Leu Leu Gln Met Asp
                805                 810                 815

Ser Glu Asp Pro Leu Val Asp Ser Ala Pro Val Thr Cys Asp Ser Glu
            820                 825                 830

Met Leu Thr Pro Asp Phe Cys Pro Thr Ala Pro Gly Ser Gly Arg Glu
        835                 840                 845

Pro Ala Leu Met Pro Arg Leu Asp Thr Asp Cys Ser Val Ser Arg Asn
850                 855                 860

Leu Pro Ser Ser Phe Leu Gln Gln Thr Cys Gly Asn Val Pro Tyr Cys
865                 870                 875                 880

Ala Ser Ser Lys His Arg Pro Ser His His Arg Thr Met Ser Asp
            885                 890                 895

Gly Asn Pro Thr Pro Thr Gly Ala Thr Ile Ile Ser Ala Thr Gly Ala
        900                 905                 910

Ser Ala Leu Pro Leu Cys Pro Ser Pro Asp Leu His Xaa His Leu Pro
        915                 920                 925

Arg Glu Val Ser Pro Lys Lys His Ser Thr Val His Ile Val Pro Gln
```

```
                930             935             940
Arg Arg Pro Ala Ser Leu Arg Ser Arg Ser Asp Leu Pro Gln Ala Tyr
945                 950                 955                 960

Pro Gln Thr Ala Val Ser Gln Leu Ala Gln Thr Ala Cys Val Val Gly
                965                 970                 975

Arg Pro Gly Pro His Pro Thr Gln Phe Leu Ala Ala Lys Glu Arg Thr
            980                 985                 990

Lys Ser His Val Pro Ser Leu Leu Asp Ala Asp Val Glu Gly Gln Ser
        995                 1000                1005

Arg Asp Tyr Thr Val Pro Leu Cys Arg Met Arg Ser Lys Thr Ser Arg
    1010                1015                1020

Pro Ser Ile Tyr Glu Leu Glu Lys Glu Phe Leu Ser
1025                1030                1035

<210> SEQ ID NO 3
<211> LENGTH: 3518
<212> TYPE: DNA
<213> ORGANISM: homo sapiens

<400> SEQUENCE: 3
gcagcgccct gggcacgacc atggtgggac gtcgcccgcg gcttcgggga ccgctgcggc      60
agcagaggcg gctggccagg aacgcgggcc gaggctggac cctttgggca gctagcccgt     120
gatctctgcc gtcaccgatc gcgattccta ccccctcgcc ttccccggc  gccgacggcc     180 acaccgccgg acgatgcgcg cccgcggccg cccgggaggc tgagcccagc ttcccgctcc     240
gccttccccg cgcagctgcc cccatggctt tgcggggcgc cgcgggagcg accgacaccc     300
cggtgtcctc ggccggggga gccccgcgcg gctcagcgtc ctcgtcgtcc acctcctcgg     360
gcggctcggc ctcggcgggc gcggggctgt gggccgcgct ctatgactac gaggctcgcg     420
gcgaggacga gctgagcctg cggcgcggcc agctggtgga ggtgctgtcg caggacgccg     480
ccgtgtcggg cgacgagggc tggtgggcag gccaggtgca gcggcgcctc ggcatcttcc     540
ccgccaacta cgtggctccc tgccgcccgg ccgccagccc cgcgccgccg ccctcgcggc     600
ccagctcccc ggtacacgtc gccttcgagc ggctggagct gaaggagctc atcggcgctg     660
ggggcttcgg gcaggtgtac cgcgccacct ggcagggcca ggaggtggcc gtgaaggcgg     720
cgcgccagga cccggagcag gacgcggcgg cggctgccga gagcgtgcgg cgcgaggctc     780
ggctcttcgc catgctgcgg cacccccaac atcatcgagct gcgcggcgtg tgcctgcagc     840
agccgcacct ctgcctggtg ctggagttcg cccgcgcgcg agcgctcaac cgagcgctgg     900
ccgctgccaa cgccgccccg gacccgcgcg cgcccggccc ccgccgcgcg cgccgcatcc     960
ctccgcacgt gctggtcaac tgggccgtgc agatagcgcg gggcatgctc tacctgcatg    1020
aggaggcctt cgtgcccatc ctgcaccggg acctcaagtc cagcaacatt ttgctacttg    1080
agaagataga acatgatgac atctgcaata aaactttgaa gattacagat tttgggttgg    1140
cgagggaatg gcacaggacc accaaaatga gcacagcagg cacctatgcc tggatggccc    1200
ccgaagtgat caagtcttcc ttgttttcta agggaagcga catctggagc tatggagtgc    1260
tgctgtggga actgctcacc ggagaagtcc cctatcgggg cattgatggc ctcgccgtgg    1320
cttatggggt agcagtcaat aaactcactt tgcccattcc atccacctgc ctgagccgtt    1380
tgccaagctc atgaaagaa  tgctggcaac aagaccctca tattcgtcca tcgtttgcct    1440
taattctcga acagttgact gctattgaag gggcagtgat gactgagatg cctcaagaat    1500
cttttcattc catgcaagat gactggaaac tagaaattca acaaatgttt gatgagttga    1560
```

-continued

```
gaacaaagga aaaggagctg cgatcccggg aagaggagct gactcgggcg gctctgcagc    1620
agaagtctca ggaggagctg ctaaagcggc gtgagcagca gctggcagag cgcgagatcg    1680
acgtgctgga gcgggaactt aacattctga tattccagct aaaccaggag aagcccaagg    1740
taaagaagag gaagggcaag tttaagagaa gtcgtttaaa gctcaaagat ggacatcgaa    1800
tcagtttacc ttcagatttc cagcacaaga taaccgtgca ggcctctccc aacttggaca    1860
aacggcggag cctgaacagc agcagttcca gtcccccgag cagccccaca atgatgcccc    1920
gactccgagc catacagttg acttcagatg aaagcaataa aacttgggga aggaacacag    1980
tctttcgaca agaagaattt gaggatgtaa aaaggaattt taagaaaaaa ggttgtacct    2040
ggggaccaaa ttccattcaa atgaaagata gaacagattg caaagaaagg ataagacctc    2100
tctccgatgg caacagtcct tggtcaacta tcttaataaa aaatcagaaa accatgccct    2160
tggcttcatt gtttgtggac cagccagggt cctgtgaaga gccaaaactt tcccctgatg    2220
gattagaaca cagaaaacca aaacaaataa aattgcctag tcaggcctac attgatctac    2280
ctcttgggaa agatgctcag agagagaatc ctgcagaagc tgaaagctgg gaggaggcag    2340
cctctgcgaa tgctgccaca gtctccattg agatgactcc tacgaatagt ctgagtagat    2400
ccccccagag aaagaaaacg gagtcagctc tgtatgggtg caccrtcctt ctggcatcgg    2460
tggctctggg actggacctc agagakcttc ataaagcaca ggctgctgaa gaaccgttgc    2520
ccaaggaaga gaagaagaaa cgagagggaa tcttccagcg ggcttccaag tcccgcagaa    2580
gygccagtcc tcccacaagc ctgccatcca cckgtgggga ggccagcagc ccaccctccc    2640
tgccactgtc aagtgccctg ggcatcctct ccacaccttc tttctccaca aagtgcctgc    2700
tgcagatgga cagtgaagat ccactggtgg acagtgcacc tgtcacttgt gactctgaga    2760
tgctcactcc ggattttgt cccactgccc caggaagtgg tcgtgagcca gccctcatgc    2820
caagacttga cactgattgt agtgtatcaa gaaacttgcc gtcttccttc ctacagcaga    2880
catgtgggaa tgtaccttac tgtgcttctt caaaacatag accrtcacat cacagacgga    2940
ccatgtctga tggaaatccg accccaactg gtgcaactat tatctcagcc actggagcct    3000
ctgcactgcc actctgcccc tcacctgmtc ytcacwgtca tctgccaagg gaggtctcac    3060
ccaagaagca cagcactgtc cacatcgtgc ctcagcgtcg ccctgcctcc ctgagaagcc    3120
gctcagatct gcctcaggct tacccacaga cagcagtgtc tcagctggca cagactgcct    3180
gtgtagtggg tcgcccagga ccacatccca cccaattcct cgctgccaag gagagaacta    3240
aatcccatgt gccttcatta ctggatgctg acgtggaagg tcagagcagg gactacactg    3300
tgccactgtg cagaatgagg agcaaaacca gccggccatc tatatatgaa ctggagaaag    3360
aattcctgtc ttaaactaag tgccttactg ttgtttaagc atttttttaa ggtgaacaaa    3420
tgaacacaat gtatctacct ttgaactgtt tcatgctgct gtgttttcaa aagctgtggc    3480
catgttccta aattagtaag atatatccag cttctcaa                           3518
```

HUMAN KINASE AND POLYNUCLEOTIDES ENCODING THE SAME

The present application is a continuation of U.S. application Ser. No. 10/014,882 filed Dec. 11, 2001 now U.S. Pat. No. 6,593,126, issued Jul. 15, 2003, which claims the benefit of U.S. Provisional application No. 60/254,744 which was filed on Dec. 11, 2000, each of which are incorporated by reference in their entirety.

1. INTRODUCTION

The present invention relates to the discovery, identification, and characterization of novel human polynucleotides encoding a protein that shares sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or overexpress the disclosed genes, antagonists and agonists of the proteins, and other compounds that modulate the expression or activity of the proteins encoded by the disclosed genes, which can be used for diagnosis, drug screening, clinical trial monitoring, the treatment of diseases and disorders, and cosmetic or nutriceutical applications.

2. BACKGROUND OF THE INVENTION

Kinases mediate phosphorylation of a wide variety of proteins and compounds in the cell. Along with phosphatases, kinases are involved in a range of regulatory pathways. Given their physiological importance, kinases have been subject to intense scrutiny and are proven drug targets.

3. SUMMARY OF THE INVENTION

The present invention relates to the discovery, identification, and characterization of nucleotides that encode a novel human protein, and the corresponding amino acid sequence of this protein. The novel human protein (NHP) described for the first time herein shares structural similarity with animal kinases, including, but not limited to, serine/threonine kinases, tyrosine kinases, TGF-beta activated kinases, and a variety of growth factor receptors. As such, the novel polynucleotides encode a new kinase protein having homologues and orthologs across a range of phyla and species.

The novel human polynucleotides described herein, encode an open reading frame (ORF) encoding a protein of 1036 amino acids in length (see SEQ ID NO: 2).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPs (e.g., expression constructs that place the described polynucleotide under the control of a strong promoter system), and transgenic animals that express a NHP sequence, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–3 are "knocked-out" they provide a method of identifying phenotypic expression of the particular gene as well as a method of assigning function to previously unknown genes. In addition, animals in which the unique NHP sequences described in SEQ ID NOS:1–3 are "knocked-out" provide a unique source in which to elicit antibodies to homologous and orthologous proteins that would have been previously viewed by the immune system as "self" and therefore would have failed to elicit significant antibody responses.

Additionally, the unique NHP sequences described in SEQ ID NOS:1–3 are useful for the identification of protein coding sequence and mapping a unique gene to a particular chromosome (the described NHP is apparently encoded on human chromosome 1, see GENBANK accession no. AL133380). These sequences identify actual, biologically verified, and therefore relevant, exon splice junctions as opposed to those that may have been bioinformatically predicted from genomic sequence alone. The sequences of the present invention are also useful as additional DNA markers for restriction fragment length polymorphism (RFLP) analysis, and in forensic biology.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequence of a novel human ORF that encodes the described novel human kinase protein. SEQ ID NO:3 describes the NHP ORF and flanking regions.

5. DETAILED DESCRIPTION OF THE INVENTION

The NHP described for the first time herein, is a novel protein that is expressed in, inter alia, human cell lines, and human fetal brain, brain, pituitary, cerebellum, lymph node, trachea, kidney, liver, prostate, testis, thyroid, adrenal gland, pancreas, stomach, small intestine, colon, skeletal muscle, heart, uterus, and fetal kidney cells. The described sequences were compiled from human genomic sequence and cDNAs made from human brain, lymph node, liver, cerebellum, kidney, testis, and bone marrow mRNAs (Edge Biosystems, Gaithersburg, Md., Clontech, Palo Alto, Calif.).

The present invention encompasses the nucleotides presented in the Sequence Listing, host cells expressing such nucleotides, the expression products of such nucleotides, and: (a) nucleotides that encode mammalian homologs of the described genes, including the specifically described NHP, and the NHP products; (b) nucleotides that encode one or more portions of the NHP that correspond to functional domains, and the polypeptide products specified by such nucleotide sequences, including but not limited to the novel regions of any active domain(s); (c) isolated nucleotides that encode mutant versions, engineered or naturally occurring, of the described NHP in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor/ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., New York, at p. 2.10.3) and encodes a functionally equivalent expression product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458 or 5,723,323 both of which are herein incorporated by reference). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar to corresponding regions of SEQ ID NO:1 (as measured by BLAST sequence comparison analysis using, for example, the GCG sequence analysis package using default parameters).

The invention also includes nucleic acid molecules, preferably DNA molecules, that hybridize to, and are therefore the complements of, the described NHP encoding polynucleotides. Such hybridization conditions can be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–3 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–3, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–3 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–3.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–3 provides detailed information about transcriptional changes involved in a specific pathway, potentially leading to the identification of novel components or gene functions that manifest themselves as novel phenotypes.

Probes consisting of sequences first disclosed in SEQ ID NOS:1–3 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–3 can be utilized in microarrays or other assay formats, to screen collections of genetic material from patients who have a particular medical condition. These investigations can also be carried out using the sequences first disclosed in SEQ ID NOS:1–3 in silico and by comparing previously collected genetic databases and the disclosed sequences using computer software known to those in the art.

Thus the sequences first disclosed in SEQ ID NOS:1–3 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–3. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence. For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation and/or as antisense primers in amplification reactions of NHP gene nucleic acid sequences. With respect to NHP gene regulation, such techniques can be used to regulate biological functions. Further, such sequences can be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a form acetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well-known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Spring Harbor Press, NY.; and Ausubel et al., 1989, Current Protocols in Molecular Biology, Green Publishing Associates and Wiley Interscience, NY.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

For example, the present sequences can be used in restriction fragment length polymorphism (RFLP) analysis to identify specific individuals. In this technique, an individual's genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from, for example, human or non-human cell lines or tissue, such as prostate, rectum, colon, or adrenal gland, known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known to, or suspected of, expressing a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well-known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, immune disorders, obesity, high blood pressure, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP sequences can then be purified and subjected to sequence analysis according to methods well-known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue may be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor, N.Y.)

Additionally, screening can be accomplished by screening with labeled NHP fusion proteins, such as, for example, alkaline phosphatase-NHP or NHP-alkaline phosphatase fusion proteins. In cases where a NHP mutation results in an expression product with altered function (e.g., as a result of a missense or a frameshift mutation), polyclonal antibodies to NHP are likely to cross-react with a corresponding mutant NHP expression product. Library clones detected via their reaction with such labeled antibodies can be purified and subjected to sequence analysis according to methods well-known in the art.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculovirus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

Where, as in the present instance, some of the described NHP peptides or polypeptides are thought to be cytoplasmic proteins, expression systems can be engineered that produce soluble derivatives of a NHP (corresponding to a NHP extracellular and/or intracellular domains, or truncated polypeptides lacking one or more hydrophobic domains) and/or NHP fusion protein products (especially NHP-Ig fusion proteins, i.e., fusions of a NHP domain to an IgFc), NHP antibodies, and anti-idiotypic antibodies (including Fab fragments) that can be used in therapeutic applications. Preferably, the above expression systems are engineered to allow the desired peptide or polypeptide to be recovered from the culture media.

The present invention also encompasses antibodies and anti-idiotypic antibodies (including Fab fragments), antagonists and agonists of a NHP, as well as compounds or nucleotide constructs that inhibit expression of a NHP sequence (transcription factor inhibitors, antisense and ribozyme molecules, or open reading frame sequence or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals can offer an advantage in that such systems allow not only for the identification of compounds that bind to the endogenous receptor/ligand of a NHP, but can also identify compounds that trigger NHP-mediated activities or pathways.

Finally, the NHP products can be used as therapeutics. For example, soluble derivatives such as NHP peptides/domains corresponding to the NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP or a protein interactive therewith. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and the corresponding deduced amino acid sequence of the described NHP are presented in the Sequence Listing. The NHP nucleotide sequences were obtained from cDNAs obtained using probes and/or primers generated from human genomic sequence.

A number of polymorphisms that may occur in the described NHP were identified including an A/G polymorphism at the nucleotide position represented by, for example, position 2182 of SEQ ID NO: 1 (which can result in a val or ile at the region corresponding to amino acid (aa) position 728 of, for example, SEQ ID NO:2), a G/T polymorphism at nucleotide position 2223 (which can result in an glu or asp at aa position 741), a G/T polymorphism at nucleotide position 2350 (which can result in a gly or cys at aa position 784), an A/C polymorphism at nucleotide position 2765 (which can result in an asp or ala at aa position 922), a C/T polymorphism at nucleotide position 2768 (which can result in a leu or pro at aa position 923), and an A/T polymorphism at nucleotide position 2773 (which can result in a ser or cys at aa position 925).

Expression analysis has provided evidence that the described NHPs are predominantly expressed in CNS tissues, and that the NHP shares significant similarity with a variety of protein kinases. Given the physiological importance of protein kinases, they have been subject to intense scrutiny as exemplified and discussed in U.S. Pat. Nos. 5,756,289 and 5,817,479 herein incorporated by reference in their entirety which additionally describe a variety of uses and applications for the described NHP.

The described NHP is apparently encoded on human chromosome 1.

The described novel human polynucleotide sequences can be used, among other things, in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus-mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell-type by following, for example, the teaching of Lasko et al., 1992, Proc. Natl. Acad. Sci. USA 89:6232–6236. The regulatory sequences required for such a cell-type specific activation will depend upon the particular cell-type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell-type, thus inactivating the endogenous NHP gene in only that cell-type, by following, for example, the teaching of Gu et al., 1994, Science, 265:103–106. The regulatory sequences required for such a cell-type specific inactivation will depend upon the particular cell-type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

5.2 NHP and NHP Polypeptides

NHP products, polypeptides, peptide fragments, mutated, truncated, or deleted forms of the NHPs, and/or NHP fusion proteins can be prepared for a variety of uses. These uses include, but are not limited to, the generation of antibodies, as reagents in diagnostic assays, the identification of other cellular gene products related to the NHP, as reagents in assays for screening for compounds that can be used as pharmaceutical reagents for the therapeutic treatment of mental, biological, or medical disorders and disease.

The Sequence Listing discloses the amino acid sequence encoded by the described NHP-encoding polynucleotides. The NHP has an initiator methionine in a DNA sequence context consistent with eucaryotic translation initiation site and a signal-like sequence indicating that the NHP can be secreted or membrane associated.

The NHP amino acid sequence of the invention include the amino acid sequence presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well-known, and, accordingly, each amino acid presented in the Sequence Listing, is generically representative of the well-known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHP products encoded by the presently described nucleotide sequences as judged by any of a number of criteria, including, but not limited to, the ability to bind and modify a NHP substrate, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions can be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where the NHP peptide or polypeptide can exist, or has been engineered to exist, as a soluble or secreted molecule, the soluble NHP peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well-known to those skilled in the art. However, such engineered host cells themselves may be used in situations where it is important not only to retain the structural and functional characteristics of the NHP, but to assess biological activity, e.g., in certain drug screening assays.

The expression systems that may be used for purposes of the invention include, but are not limited to, microorganisms such as bacteria (e.g., E. coli, B. subtilis) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing NHP nucleotide sequences and promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target expression product can be released from the GST moiety.

In an insect system, *Autographa californica* nuclear polyhedrosis virus (AcNPV) is used as a vector to express foreign polynucleotide sequences. The virus grows in *Spodoptera frugiperda* cells. A NHP coding sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46: 584; Smith, U.S. Pat. No. 4,215,051).

In mammalian host cells, a number of viral-based expression systems can be utilized. In cases where an adenovirus is used as an expression vector, the NHP nucleotide sequence of interest may be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler et al., 1977, Cell 11:223), hypoxanthine-guanine phosphoribosyltransferase (Szybalska and Szybalski, 1962, Proc. Natl. Acad. Sci. USA 48:2026), and adenine phosphoribosyltransferase (Lowy et al., 1980, Cell 22:817) genes, which can be employed in tk$^-$, hgprt$^-$ or aprt$^-$ cells, respectively. Also, antimetabolite resistance can be used as the basis of selection for the following genes: dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147). Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto Ni$^{2+}$-nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in "Liposomes: A Practical Approach", New, R.R.C., ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. applications Ser. Nos. 60/111, 701 and 60/056,713, both of which are herein incorporated by reference, for examples of such transducing sequences) to facilitate passage across cellular membranes and can optionally be engineered to include nuclear localization.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention can be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP expression product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including, but not limited to, Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diphtheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, *Nature* 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal, Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used (see U.S. Pat. Nos. 6,075,181 and 5,877,397 both of which are herein incorporated by reference in their entirety). A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to: F(ab')$_2$ fragments, which can be produced by pepsin digestion of the antibody molecule; and Fab fragments, which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well-known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor/ligand can be used to generate anti-idiotypes that "mimic" the NHP and, therefore, bind, activate, or neutralize a NHP, NHP receptor, or NHP ligand. Such anti-idiotypic antibodies or Fab fragments of such anti-idiotypes can be used in therapeutic regimens involving a NHP-mediated pathway.

Additionally given the high degree of relatedness of mammalian NHPs, the presently described knock-out mice (having never seen NHP, and thus never been tolerized to NHP) have a unique utility, as they can be advantageously applied to the generation of antibodies against the disclosed mammalian NHP (i.e., NHP will be immunogenic in NHP knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. A substantially isolated polypeptide comprising the amino acid sequence of SEQ ID NO: 2.

* * * * *